United States Patent
High et al.

(10) Patent No.: US 10,803,148 B2
(45) Date of Patent: Oct. 13, 2020

(54) METHOD AND SYSTEM FOR MOTIVATING PROPER PRESCRIPTION DRUG USAGE

(71) Applicant: Walmart Apollo, LLC, Bentonville, AR (US)

(72) Inventors: Donald R. High, Noel, MO (US); Nicholas D. Rone, Bella Vista, AR (US)

(73) Assignee: WALMART APOLLO, LLC, Bentonville, AR (US)

( * ) Notice: Subject to any disclaimer, the term of this patent is extended or adjusted under 35 U.S.C. 154(b) by 1016 days.

(21) Appl. No.: 15/062,540

(22) Filed: Mar. 7, 2016

(65) Prior Publication Data

US 2016/0267249 A1 Sep. 15, 2016

Related U.S. Application Data

(60) Provisional application No. 62/132,745, filed on Mar. 13, 2015.

(51) Int. Cl.
*G06F 19/00* (2018.01)
*G16H 20/10* (2018.01)

(52) U.S. Cl.
CPC ......... *G06F 19/3456* (2013.01); *G16H 20/10* (2018.01)

(58) Field of Classification Search
CPC ..... G06F 19/3456; G06F 19/00; G16H 20/10; G16H 20/60; G16H 20/70; G16H 20/90; G16H 40/67

(Continued)

(56) References Cited

U.S. PATENT DOCUMENTS

| 5,842,976 A | 12/1998 | Williamson |
| 6,003,006 A | 12/1999 | Colella et al. |

(Continued)

FOREIGN PATENT DOCUMENTS

| EP | 1025528 | 8/2008 |
| EP | 2489149 | 8/2012 |

(Continued)

OTHER PUBLICATIONS

"MedCoach Medication Reminder: version 1.8", iTunes.apple.com, Sep. 19, 2013, GreatCall, Inc., accessed on Dec. 22, 2016; 2 pages.

(Continued)

*Primary Examiner* — Jonathan Durant
*Assistant Examiner* — Gregory D. Moseley
(74) *Attorney, Agent, or Firm* — Schmeiser, Olsen & Watts LLP; Timothy P. Collins

(57) ABSTRACT

A system and method includes: a pharmacy server receiving a customer ID code to allow a customer wireless access to his medical data file stored on the server; the server receiving compliance determination data to determine whether the customer is taking prescription medicine according to directions; activating a shell script on the wireless device from the server when the compliance determination data indicates that the customer is taking the medicine properly; and de-activating the shell script on the wireless device when the compliance determination data indicates that the customer is not taking the medicine properly, whereby the shell script provides wireless operation of a software application.

20 Claims, 5 Drawing Sheets

(58) Field of Classification Search
USPC .......................................................... 705/2, 3
See application file for complete search history.

(56) References Cited

U.S. PATENT DOCUMENTS

| | | | |
|---|---|---|---|
| 7,032,026 | B1 | 4/2006 | Biswas et al. |
| 7,630,908 | B1 | 12/2009 | Amrien et al. |
| 7,975,292 | B2 | 7/2011 | Corella |
| 8,005,688 | B2 | 8/2011 | Coffman et al. |
| 8,302,187 | B1 | 10/2012 | Gupta et al. |
| 8,392,220 | B2 | 3/2013 | Knowlton et al. |
| 9,852,261 | B1* | 12/2017 | Havard .................. G06F 19/00 |
| 2003/0105555 | A1 | 6/2003 | Lunak et al. |
| 2003/0140928 | A1 | 7/2003 | Bui et al. |
| 2006/0136272 | A1 | 6/2006 | Rubsamen |
| 2008/0030309 | A1 | 2/2008 | Darrouzet |
| 2008/0059242 | A1 | 3/2008 | Stanford |
| 2008/0313721 | A1 | 12/2008 | Corella |
| 2009/0192648 | A1 | 7/2009 | Namineni et al. |
| 2010/0324936 | A1 | 12/2010 | Vishnubhatla et al. |
| 2011/0015945 | A1 | 1/2011 | Addy |
| 2011/0066260 | A1 | 3/2011 | Condurso et al. |
| 2011/0184755 | A1 | 7/2011 | Yamaga et al. |
| 2011/0226651 | A1 | 9/2011 | Patino |
| 2012/0303388 | A1 | 11/2012 | Vishnubhatla et al. |
| 2013/0054271 | A1 | 2/2013 | Langford et al. |
| 2013/0253291 | A1 | 9/2013 | Dixon et al. |
| 2013/0317840 | A1* | 11/2013 | Creswell ............ G06F 19/3456 705/2 |
| 2014/0039672 | A1 | 2/2014 | Evondos Oy |
| 2014/0039911 | A1 | 2/2014 | Iyer |
| 2014/0058561 | A1 | 2/2014 | Rothschild |
| 2014/0089011 | A1 | 3/2014 | Fletcher |
| 2014/0142979 | A1 | 5/2014 | Mitsunaga |
| 2014/0188502 | A1 | 7/2014 | Defrank et al. |
| 2014/0236617 | A1* | 8/2014 | Oberfest ............. G06F 19/3456 705/2 |
| 2014/0277705 | A1 | 9/2014 | Czaja et al. |
| 2014/0350720 | A1 | 11/2014 | Lehmann et al. |
| 2014/0350949 | A1 | 11/2014 | Utech et al. |
| 2015/0332017 | A1* | 11/2015 | Swanson ................ G16H 50/20 705/3 |
| 2016/0055698 | A1* | 2/2016 | Gudmundsson ... G07C 9/00142 340/5.52 |

FOREIGN PATENT DOCUMENTS

| | | |
|---|---|---|
| JP | 2013168820 | 8/2013 |
| KR | 20130038319 | 4/2013 |
| WO | 2003098399 | 11/2003 |
| WO | 2014037850 | 3/2014 |
| WO | 2014159933 | 10/2014 |

OTHER PUBLICATIONS

"Scan", Clinicate.com, 2014, Clinicate, LLC, accessed on Dec. 22, 2014; 4 pages.
Wideman, Mary V., et al. "Barcode Medication Administration: Lessons Learned from an Intensive Care Unit Implementation", Advances in Patient Safety vol. 3, FDA.gov, Feb. 2005, accessed on Dec. 22, 2014; 16 pages.
"Walgreens—Android Apps on Google Play", Play.Google.com, Nov. 6, 2014, Walgreen Co., accessed on Dec. 19, 2014; 2 pages.
"Search the Lowest Drug Price", LowestMed.com, updated 2014, LowestMed, first accessed on Dec. 19, 2014, most recently accessed Mar. 4, 2016; 1 page.
"How GoodRx Works", GoodRx.com, 2014, GoodRx, Inc., accessed on Dec. 19, 2014; 3 pages.
Dolan, Brian, "Walgreens app adds pill reminders, Rx transfer", Mobihealthnews.com, Mar. 12, 2012, accessed on Feb. 3, 2015; 3 pages.

* cited by examiner

METHOD AND SYSTEM FOR MOTIVATING PROPER PRESCRIPTION DRUG USAGE

RELATED APPLICATIONS

This application claims priority to U.S. Provisional Application Ser. No. 62/132,745, filed on Mar. 13, 2015 entitled "METHOD AND SYSTEM FOR MOTIVATING PROPER PRESCRIPTION DRUG USE", the entirety of which is incorporated by reference herein.

FIELD OF THE INVENTION

A system and method are described herein for monitoring whether a customer of a pharmacy who receives prescription medicine takes his medicine in accordance with instructions, rewarding the customer when he correctly takes his medicine and penalizing the customer when he does not take his medicine properly. More specifically the customer is rewarded for compliance in taking his medicine properly by receiving access to a computer application on the customer's wireless computer device, and he is penalized by being denied access to the computer application for non-compliance in taking his medicine properly.

BACKGROUND

The proper usage of prescription medicines is important for improvement of a person's health and for accurate diagnosis and analysis of the person's ongoing symptoms by a doctor, nurse or other caregiver. Monitoring the proper prescription dosages along with comparing the improvement or failing of the person's health allows the doctor to adjust the medicine for the benefit of the individual.

Organizations, such as insurance companies, also need a way to encourage their customers to stay on and consistently take their medications at the right time. They often provide tools for their customers to remind them to take their medication but these tools are sometimes used for other purposes than intended. Organizations need a way of providing tools and encouraging the proper use of medications in order to promote public health and to contain the costs of medical care. If a customer does not properly take his medicine, then it is likely that his condition will worsen which, in turn, will end up costing the insurance company and everyone more in the long run.

Most medicine dispensing systems intended for a personal use consist of a daily, weekly, etc. container with instructional information describing the proper dosage of each medication to be dispensed at each dispensing period. Another type of medicine dispensing system for a personal use consists of a programmable device similar to an alarm clock for reminding the patient when to take their next medication.

In recent years, the use of mobile devices such as smart phones having Internet access has become popular, especially among younger people. As a result, cellular telephones or other wireless devices, installed in primary residences, are considered as candidates to provide various health care-monitoring and even health care-delivering functions. Considering that strict adherence to the timely dispensing of medication is critical to the quality of provided health care, combining of simple dispensing mechanism with the ubiquitous cellular phone can provide the benefits of virtual medical supervision of the medication dispensing regime at very low cost.

Improvements are desired for a method and system to motivate and monitor proper prescription drug usage for a customer receiving a prescription at a pharmacy.

BRIEF SUMMARY OF EMBODIMENTS

A system and method for motivating proper prescription drug usage includes: a pharmacy server receiving a customer ID code to allow a customer wireless access to his medical data file stored on the server; the server receiving compliance determination data to determine whether the customer is taking prescription medicine according to directions; activating a shell script on the wireless device from the server when the compliance determination data indicates that the customer is taking the medicine properly; and de-activating the shell script on the wireless device when the compliance determination data indicates that the customer is not taking the medicine properly, whereby the shell script provides wireless operation of a software application resident on the customer's wireless device, on the pharmacy server or at another URL address available on the Internet.

A method for motivating proper prescription drug usage includes the steps of: receiving at a server for a pharmacy, via wireless communications from a wireless device, an ID code corresponding to a customer who has received prescription medicine from the pharmacy; providing access by the wireless device to a medical data file of the customer on the server when the ID code is authenticated; receiving compliance determination data from the wireless device to determine whether the customer is taking the prescription medicine in accordance with a predetermined schedule; and activating a shell script on the wireless device from the server when the compliance determination data indicates that the customer is taking the prescription medicine in accordance with the schedule, and de-activating the shell script on the wireless device when the compliance determination data indicates that the customer is not taking the prescription medicine in accordance with the schedule, wherein the shell script provides wireless operation of a software application that is resident on the customer's wireless device, on the pharmacy server or at another URL address available on the Internet.

A system for motivating proper prescription drug usage includes: a server for providing computer services to a pharmacy for creating and storing a medical data file for a customer in a database on the server when a prescription for the customer is filled for a medicine into a container and supplying to the customer the prescription container along with an ID code linked to the customer's medical data file and instructions for taking the medicine; a receiving unit connected to the server to receive data via wireless communications over the Internet from a wireless device of the customer, the received data including the ID code to authenticate and establish communications between the customer's wireless device and the server, wherein the received data further includes compliance determination data to determine whether the customer is taking the prescription medicine according to the instructions; and a transmitting unit connected to the server to transmit data via wireless communications over the Internet from the server to the customer's wireless device, the transmitted data including a shell script linked to a software application resident on the customer's wireless device, on the pharmacy server or at another URL address available on the Internet, wherein the transmitted data further includes data to activate the shell script on the customer's wireless device when the compliance determination data indicates compliance in the customer taking the medicine, and data to de-activate the shell script on the customer's wireless device when the compliance determination data indicates non-compliance in the customer taking the medicine.

The above and other aspects of various embodiments will become apparent in view of the following description, claims and drawings.

BRIEF DESCRIPTION OF THE SEVERAL VIEWS OF THE DRAWINGS

The accompanying drawings, in which like numerals indicate like structural elements and features in various figures, are not necessarily drawn to scale.

DETAILED DESCRIPTION

In the following description, specific details are set forth although it should be appreciated by one of ordinary skill that the systems and methods can be practiced without at least some of the details.

A patient under medical care from a doctor whether at home, at a hospital or at another caregiving facility will require medication as prescribed and/or recommended by the doctor or other caregiver who is qualified to prescribe medicine. After a pharmacy fills a prescription for a customer (i.e. the doctor's patient), he will either pick up the prescription himself, have it sent to him, or have a caregiver such as a private nurse pick up the prescription for him.

Figure 1:
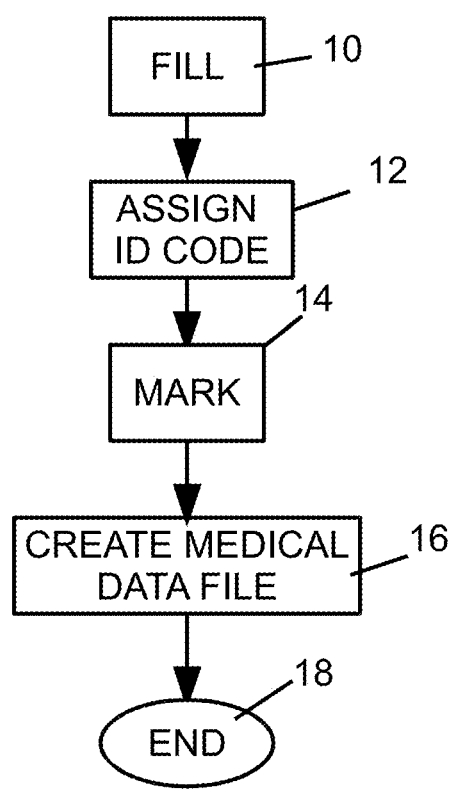
FIG. 1 is a flow chart diagram of a method for filling a prescription for a customer at a pharmacy and creating a medical data file for the customer on a server of the pharmacy.

In the flow chart diagram of FIG. 1 a method is shown for filling a medical prescription for a customer at a pharmacy and creating a medical data file for the customer on a server of the pharmacy. When filling a prescription for a medicine, a pharmacist places the prescribed medicine into a bottle or other appropriate container as indicated in block 10. Of course the medicine could be in pill form, liquid form, in a syringe, or in any other form as prescribed by a doctor. The prescription could also be directed towards any sort of medical device prescribed by a doctor and available from a pharmacy.

In block 12 a customer ID code is assigned to a new customer. If the customer is an existing customer, then preferably the same ID code will be used by the customer for all prescription data belonging to the customer at the pharmacy. Alternatively, a separate ID code could be assigned to the customer for each separate prescription.

In block 14 the customer's ID code is printed or otherwise marked or added to the container, to a label on the container, or onto an attached document such as instructions for taking the medicine. The primary purpose of the ID code is to link and uniquely identify the filled prescription of a customer to a customer's medical data file stored on a server for a pharmacy.

The customer's medical data file is originally set up by the pharmacist and can include information such as, but not limited to: the customer's name, telephone number, email and postal address; the name and dosage of the prescribed medicine; instructions for taking the medicine including one or more predetermined tolerances for taking the medicine; and, a name and contact information of a doctor who prescribed the medicine. Eventually, the customer's medical data file will be appended to include other information such as: the customer's compliance determination data which is a recordation of whether the customer is taking the medicine properly according to the instructions; and the customer's prescription medicine history including compliance determination data for taking previously prescribed medicines.

Turning back to FIG. 1, in block 14 the ID code and the label for the container are preferably printed at the same time to ensure that the correct ID code is attached to, marked upon, or otherwise accompanying, the container for each individual prescription. Any type of ID code can be used that can be accessed by way of any known method, such as but not limited to, a scannable barcode, a QR code, a magnetic strip code, an OCR (optical character recognition code), an encrypted code, standard alpha-numerical characters, a code identifiable by digital imaging, or any other code. A label marking device, such as a printer or dedicated label marking machine, can be used to mark the ID code and directions onto the container, onto a label to be affixed to the container, or onto a separate piece of paper accompanying the container of medicine.

The ID code can be a set of alpha-numerical characters that can be read by the customer, or preferably it is an encrypted machine readable code. For example, an ID code can be a QR code which is a type of matrix barcode or two dimensional barcode consisting of an array of black and white squares, typically used for storing URLs or other information to be read by a camera on a smartphone.

One example of a machine code-reading device is a barcode reader or scanner which is an electronic device for reading printed barcodes such as a barcode or QR code from the label of the container. The barcode reader consists of a light source, a lens and a light sensor for translating optical impulses into electrical pulses.

If the prescription being filled is for a new customer, then in block 16 a new medical data file is created, linked for access to the customer's ID code and stored in a database on the pharmacy computer/server. If a medical data file for the customer already exists in the database, then the new prescription data is added to the customer's existing medical data file in block 16. The pharmacist can also set up login information for a new customer such as an user name and password to allow the customer, after the prescription has been filled, to be able to login at a pharmacy website available on the Internet. Alternately, the customer could use his assigned ID code along with his name and/or other identifying data on the pharmacy website to create a new account and select an user name and password. The process shown in FIG. 1 ends in block 18, and the customer can thereafter use his assigned customer ID code to access his or her medical data file at any time by wireless communications over the Internet.

The medical data files of prescription records for pharmacy customers can be stored (as shown for example in FIG. 6) in a database 126 located on a server 120 located within the pharmacy, or they can be accessed and stored on a remote server by wireless communications over the Internet 140. The remote server can be located, for example, in a separate room of the pharmacy, at a separate location servicing the pharmacy, at a store headquarters, or any other location.

When the pharmacist receives a prescription from a new customer, the pharmacist will enter the customer's personal information such as (but not limited to) his or her name, address and phone number which is input from a pharmacist's workstation 132 into the pharmacy's computer system 142 (see FIG. 6). A software application resident on the pharmacy's server will provide an user interface on the workstation 132 so that the pharmacist can enter and retrieve data from the pharmacy server 120. The software application will assign an unique ID code to the customer and will create an unique medical data file 130 in the database 126 for the customer which is accessible via the customer's ID code. Other security codes and measures can be implemented to further secure the customer's medical data file and if the customer loses the ID code, then the pharmacist can access the customer's medical data file using the customer's personal information such as his name, telephone number, or social security number. In addition to the customer's personal information, the pharmacist can enter other information in predetermined entry fields mapped to the customer's medical data file 130 such as information identifying the customer's prescribed medicine, dosage, and the name of the doctor who is prescribing the medication. The medicine is typically prescribed for a specific time period and a specific number of refills, such as 30 pills to be refilled once a month for a period of one year.

For each medicine prescribed to a customer, the customer receives instructions for taking the medicine which includes guidelines and tolerances, set by the customer's doctor, for proper care, usage and administration of the medicine. The tolerance levels are preset margins of error that are acceptable for proper administration of the medicine such as setting a window of time for when to take the medication for maximum effectiveness. Other guidelines can include the dosage of the medicine which can be adjusted by the number of pills or spoonfuls of liquid medicine taken at one time, whether to take the medicine with food or water, etc. The guidelines and tolerances are all predetermined by the doctor according to the specific needs of the customer for whom the medicine is prescribed.

For example, a prescription may be filled for a customer who is required to take one pill twice a day, once in the morning after breakfast and the second time in the early evening after a meal. Let us assume that the effectiveness of the medicine is maximized if the pills are taken at 12 hour intervals and the pills are still relatively effective if taken within 8 to 14 hours of one another. Also, let's assume that damage to the customer's stomach lining could occur if the medicine is not taken immediately after or during a meal. In this case, the tolerances could be set to taking one pill in the morning during or immediately after breakfast between 7-10 am, and one pill in the evening during or immediately after dinner between 7-10 pm.

When the customer is taking the medicine either he, or a caregiver responsible for overseeing that the customer takes the medicine, can access the customer's medical data file on the pharmacy server using wireless communications. Of course only the customer can have access to the pharmacy server and his medical data file which is secured by the customer's ID code as well as standard security measures including an user name and password. When the customer logs on to the pharmacy server the first time, he can be asked to register his wireless device as an additional security measure, for example, by allowing the pharmacy server to poll the Internet Protocol (IP) address of the wireless device. Thereafter, only communications received from the customer's registered wireless device will be allowed access to the server or the customer's medical data file.

If the customer is unable to communicate via a wireless device, then an authorized caregiver (such as a nurse or a spouse) can be granted permission to access the customer's medical data file in order to submit adherence confirmation data to taking the medicine. Any type of known wireless communications device can be used to communicate over the Internet, such as but not limited to a smart phone, a tablet, a desktop computer, a laptop computer, etc.

After taking his/her medicine, the customer or his authorized caregiver can log onto the pharmacy server and access the customer's medical data file using the customer's ID code. A single ID code could be provided to the customer for all of his prescriptions, or a separate ID code could be provided to the customer for each separate prescription. In either alternative, the customer's ID code(s) allow online access to the customer's medical data file.

Figure 2:
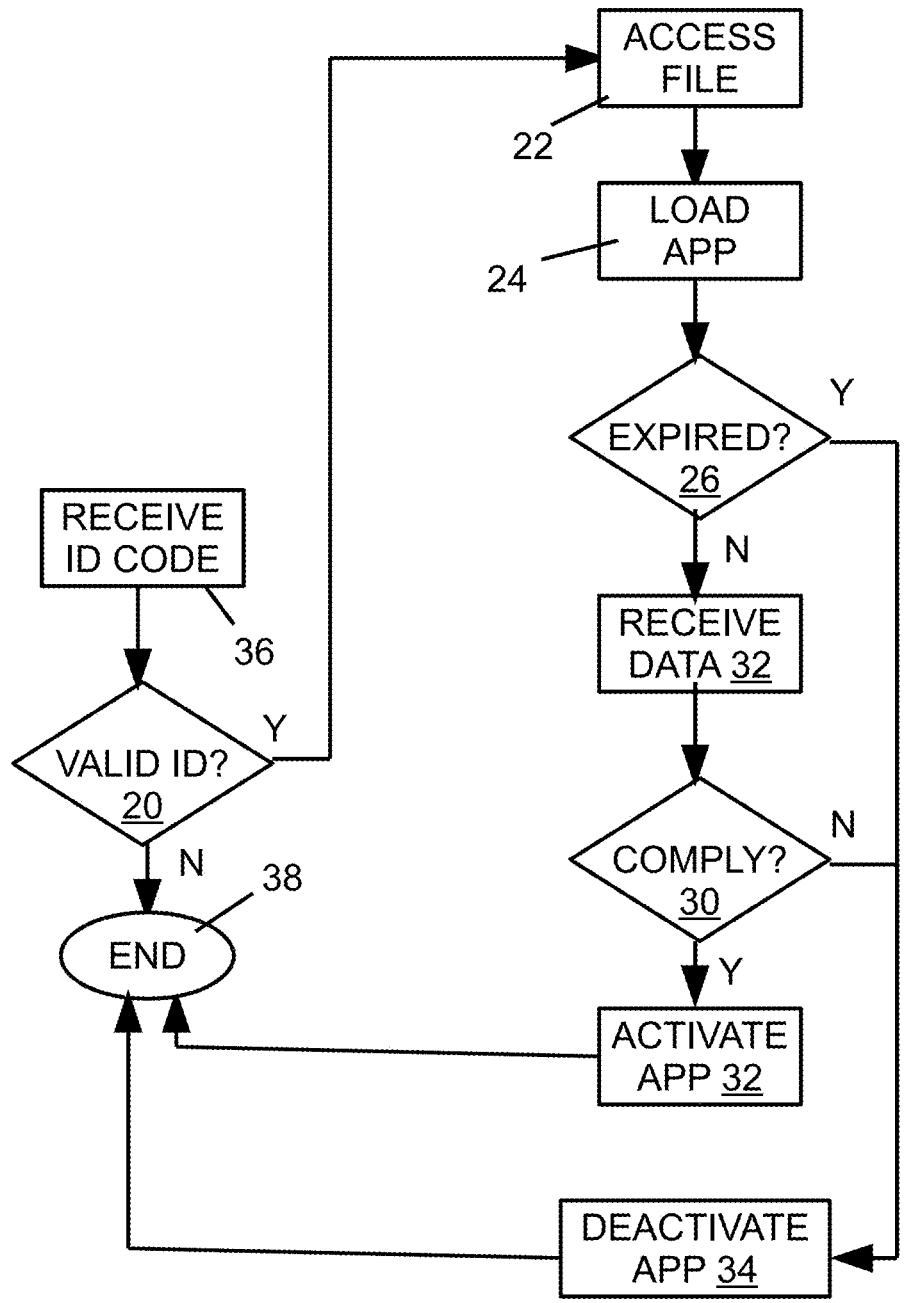
FIG. 2 is a flow chart diagram of a first embodiment of a method for monitoring the usage of a prescription drug received by a customer from a pharmacy and motivating the customer's proper intake of the prescribed medicine.
Figure 5:
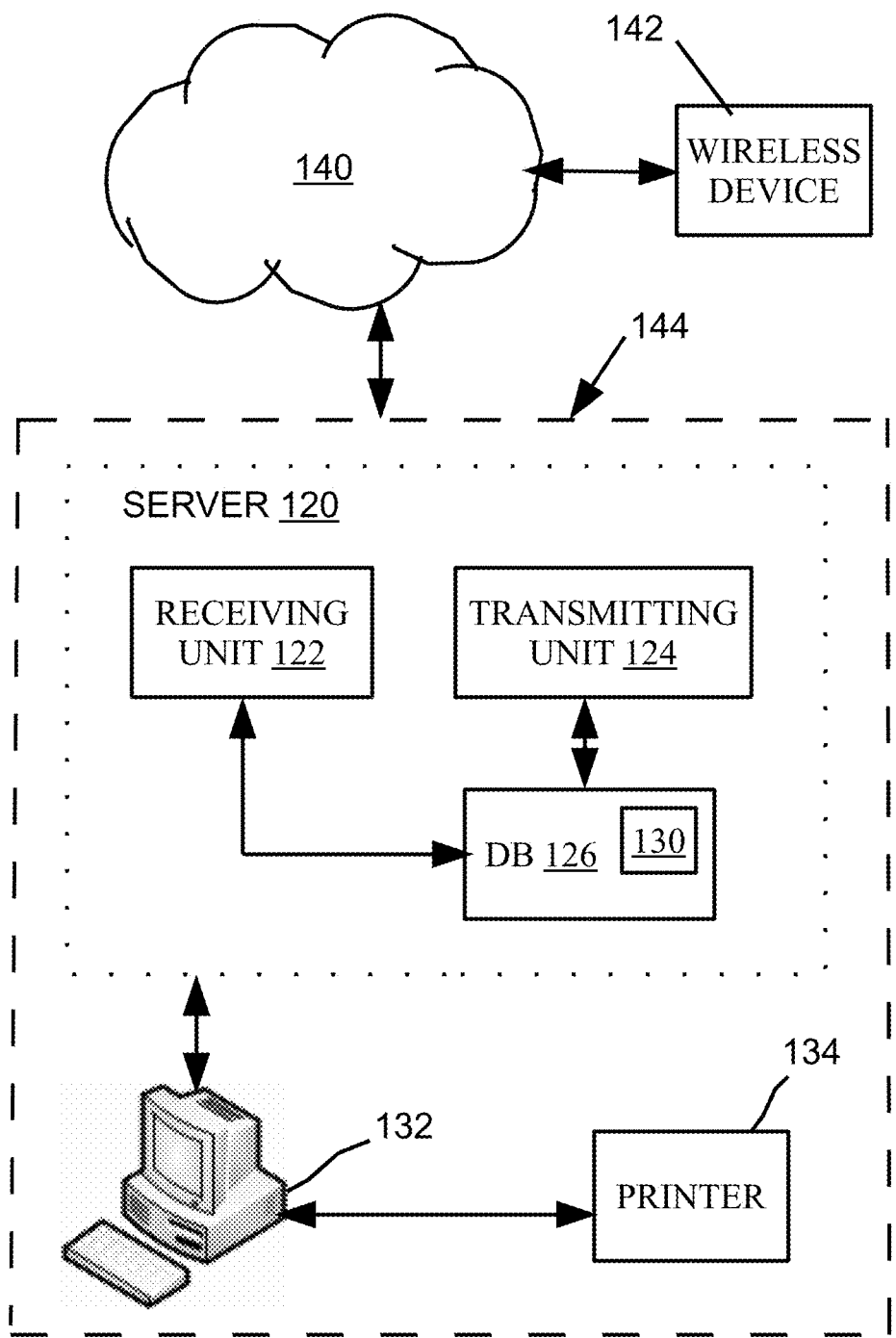
FIG. 5 is an alternative diagrammatic representation of an architecture of a wireless communications system.

The flow chart diagram of FIG. 2 shows a first embodiment of a method for monitoring the usage of a prescription drug received by a customer from a pharmacy and motivating the customer's proper intake of the prescribed medicine. In step 36 the ID code is received by the pharmacy server over the Internet via online wireless communications from a wireless device to which the customer has access. A determination is made in decision block 20 whether the ID code received online by the customer is valid. In other words, a determination is made whether the received ID code corresponds with other received authentication information such as the customer's name, address or social security number. If the ID code is determined to be invalid or incorrect in decision block 20, then the process ends in block 38. If the ID code is verified in block 20, then access is allowed in block 22 to the customer's medical data file 130 stored in the database 126 of the pharmacy server 120 as shown in FIG. 5.

The first time that the customer logs onto his pharmacy account to access his medical data file after receiving his prescription medicine, the customer can choose to load one of a number of available software applications (i.e. an "app") listed on the pharmacy server to his wireless device, whether it be a smart phone, a desktop computer, a laptop computer, a computer tablet or the like (see FIG. 2, block 24). The software application can be a shell script of instructions that controls access to an application resident on the pharmacy server. The selection of software applications includes, but is not limited to: a gaming application; an entertainment application; an application allowing accessibility to an online service; an application allowing accessibility to special features of an online service; an application for watching movies; an application for watching videos; an application for listening to music; an application to enhance social network services; and an application to enhance online communications. The available software applications can be resident on the pharmacy server, on the customer's wireless device, or at another URL address (i.e. an Uniform Resource Locator or address of a web page) available on the Internet.

The applications made available from the server for the customer to download are catered towards being desirable applications that are otherwise not readily available to the customer without him paying a fee. For instance, one application can allow the customer a temporary membership to www.vudu.com which is a video on demand website where movies and television shows can be rented or purchased. The application would give the customer free access, or a free membership to the movies and shows on the website for the duration of time in which his prescription is valid.

Various online games and game services can also be made available for selection by the customer, such as a game that requires a fee or membership through a third party website. Also, a stand alone game that doesn't require an Internet connection could be loaded onto the customer's smart phone or other wireless device from the pharmacy server or from another website. A shell script could also be loaded from the server onto the customer's smart phone or other wireless device, whereby the server would be able to communicate with the shell script in order to activate or de-activate the application loaded onto the customer's wireless device. The available applications could also include online memberships, or accessibility to an online service such as, but not limited to, a tutorial on how to play a musical instrument, a discount travel club, etc. Another example is an application to enhance social network services such as an application that can be used on Facebook, Snap Chat, Twitter, ReverbNation or any other online social network. Any stand alone, or online entertainment application that is made available from the pharmacy website can be featured and accessible for download by the customer.

Turning back to the method of FIG. 2, a determination is made in decision block 26 whether the prescription has expired. The expiration date of the medicine is initially input into the customer's medical data file when the pharmacist fills the prescription. If the expiration date has been reached, then any program/application/shell script running on the customer's wireless device is deactivated in block 34 and the process ends in block 38. If the expiration date of the medicine has not been reached, then the customer can next submit adherence confirmation data which is received by the server in block 32.

The compliance determination data, also referred herein as the adherence confirmation data or compliance confirmation data, is used to determine compliance by the customer in taking his medicine according to the instructions. The adherence confirmation data can either accompany the ID code, or preferably be entered and subsequently submitted by the customer and received from the customer's wireless device after permission is granted to access the customer's medical data file. The customer can send the adherence confirmation data, for example, by filling in required data entry fields of an adherence confirmation interface made available to the customer on his wireless device from the pharmacy server, and including information such as the time and date that the medicine was taken, the dosage taken, the name of the medicine taken, and/or any other required adherence confirmation data as required for the specific prescription.

The adherence confirmation interface can run as an app (i.e. a software application) from a shell program that is loaded from the pharmacy server onto the customer's wireless device, or the adherence confirmation software can run directly on the pharmacy server. The application can request or even require a second confirmation such as by e-signature from a second party such as a caregiver, spouse, or other person who witnesses that the customer took his medication as reported to the pharmacy.

The pharmacy server checks, as shown in decision block 30 of FIG. 2, the adherence confirmation data that was received from the customer's wireless device in block 32 and determines whether the received data confirms or denies adherence within the preset tolerances of complying with taking the medicine according to the instructions. If compliance is negated, then an application running on the customer's wireless device will be deactivated through its shell script as indicated in block 34. If compliance is confirmed, then an existing application running of the customer's wireless device will be allowed to continue through its shell script, and any first time installed shell script application on the wireless device will be activated. The process ends in block 38.

In the above example, the time and date entered by the customer or caregiver to indicate when the medicine was taken is considered as the adherence confirmation data. However, the adherence confirmation data can be set and defined by the customer's doctor for confirming that the medicine is properly taken by the customer according to the instructions accompanying the prescription, and could include information such as, but not limited to, (1) the time at which the medicine is taken, (2) the dosage of the medicine taken, (3) the number of pills taken, (4) whether the medicine was taken with food or drink, (5) a dual confirmation by both the customer and another person such as the caregiver of the information reported to the pharmacy server, and (6) whether the prescribed medicine was taken simultaneously with other medicine, etc.

Figure 3:
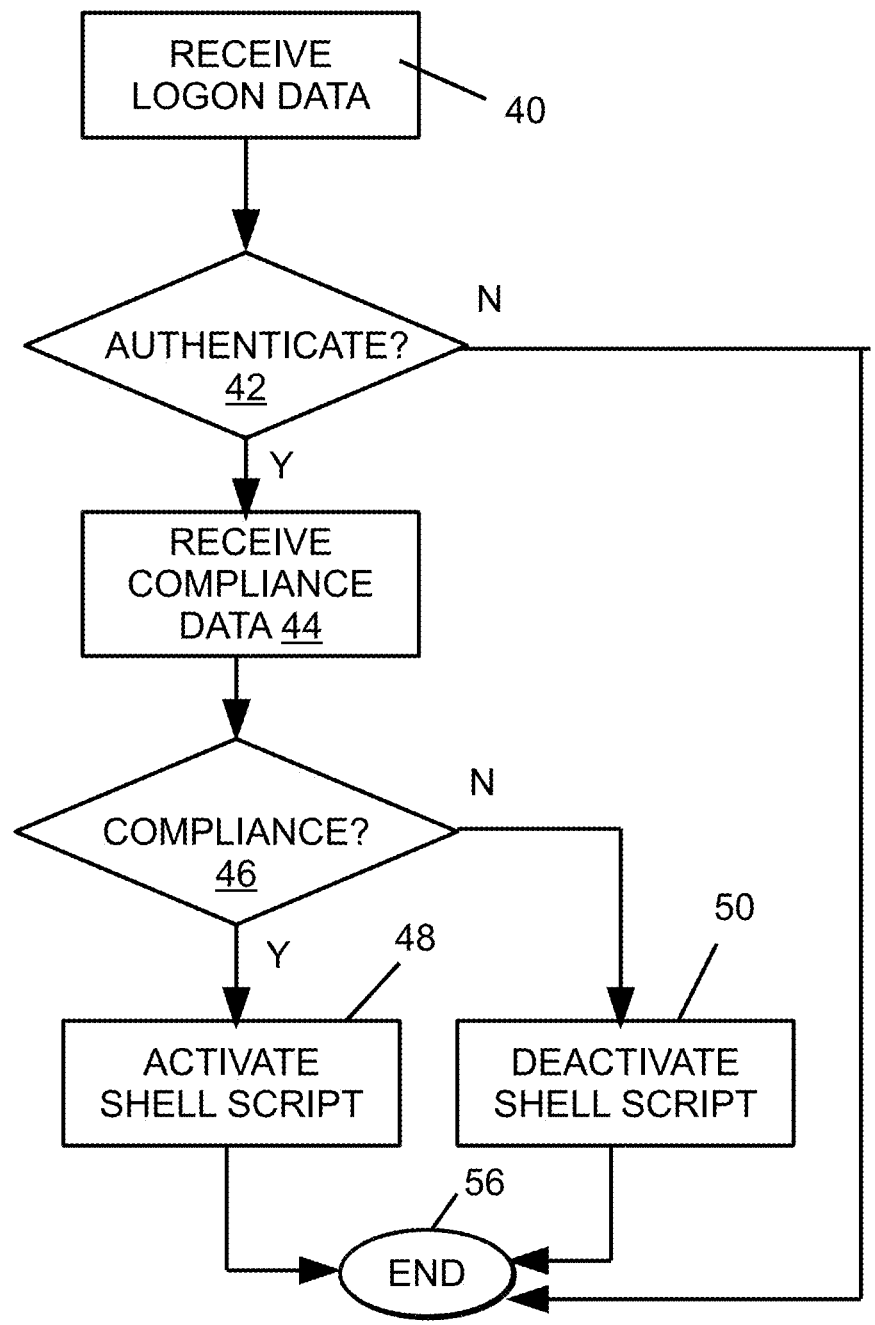
FIG. 3 is a flow chart diagram of a second embodiment of a method for monitoring the usage of a prescription drug received by a customer from a pharmacy and motivating the customer's proper intake of the prescribed medicine.

FIG. 3 is a flow chart diagram of a second embodiment of a method for monitoring the usage of a prescription drug received by a customer from a pharmacy and motivating the customer's proper intake of the prescribed medicine. In block 40 a customer ID code is received online, from a wireless device to which the customer has access via wireless communications, by the pharmacy server along with other logon security data such as an user name and password to allow the customer's wireless device to logon to the pharmacy server. The pharmacy server will authenticate the logon data in decision block 42. If the logon information is incorrect, then the process ends in block 56. If the logon information is correct, then the customer submits the adherence confirmation data in block 44 which is received by the pharmacy server to confirm that he has taken the medicine within the predetermined tolerances according to the instructions for the prescription. If compliance for taking the medicine within the tolerances is confirmed in decision block 46, then the shell script that was previously loaded onto the customer's wireless device (upon receipt of the prescription medicine and as an incentive for properly taking the medicine) is activated or remains activated in block 48. In other words, the customer is rewarded for complying with the instructions for properly taking his/her medicine. If the customer was non-compliant in taking the medicine, then the shell script on the customer's wireless device is deactivated by communications from the server in block 50. The process ends in block 56.

A report application can also be made available on the pharmacy server to allow access by the customer to receive or send a report which could include information such as the history of the customer's compliance in taking his medicine. The report could be presented in any convenient format, such as in a graphical or tabular form, and could include historical customer information including the customer's compliance determination data, dates of reported compliance or non-compliance, etc. The report could also be used to provide an analysis of the customer's medical data file that could be sent via wireless communications (or as written reports via postal mail) to one or more of the customer, a pharmacist, a doctor, a nurse, a caregiver, an insurance company, a hospital or others involved in the prescribing, distributing, maintaining, monitoring and administering of the prescription medicines of the customer. The above report(s) could be automatically scheduled to run and distributed to a list of recipients at predetermined time intervals such as once a month via a software program on the server, or the report program could be manually selected and run by the customer.

Notifications regarding the prescribed medicine can be sent at any time as emails via wireless communications from the server (or by postal mail) to one or more of the customer, a pharmacist, a doctor, a nurse, a caregiver, an insurance company, a hospital or others involved in the prescribing, distributing, maintaining, monitoring and administering of the medicine to the customer. The notifications can be automatic alerts occurring at predetermined intervals such as once a month and the notifications can include, but are not limited to, reminders for the customer to take his medicine, that the prescription medicine is about to expire, or to contact the pharmacy for a refill. The notifications can also be sent manually by a pharmacist from the pharmacy.

Figure 4:
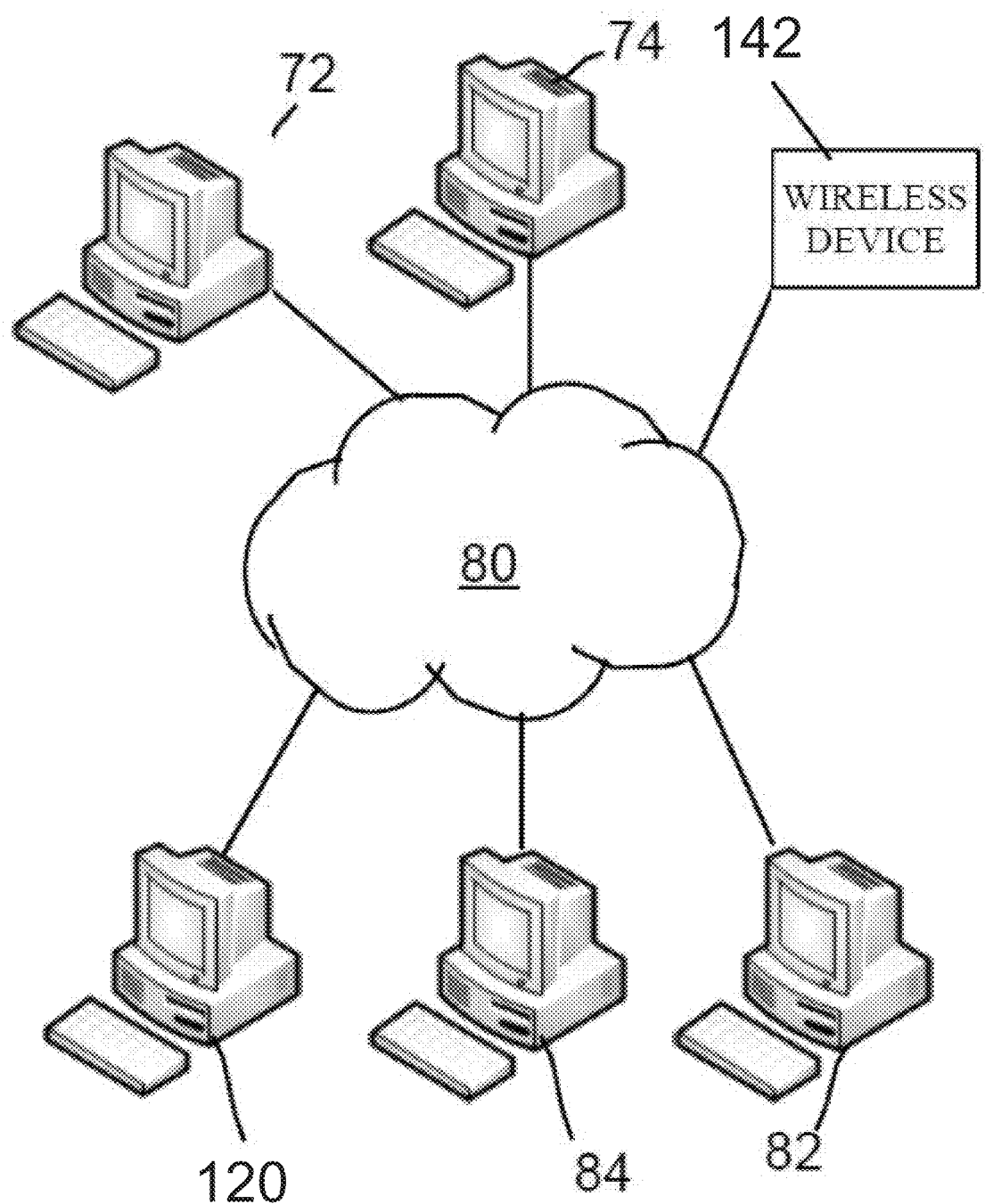
FIG. 4 is a diagrammatic representation of a wireless communications system architecture.

FIG. 4 illustrates a typical wireless network whereby computers 72, 74, 82, 84 and 120 and a smart phone 142 or any other wireless device can communicate wirelessly with one another over the Internet network 80. In this example, the customer could use the smart phone 142 to communicate with the pharmacy server 86 via the Internet 80 to access the customer's medical data file resident on the pharmacy server.

FIG. 5 illustrates an alternative diagrammatic representation of an architecture of a wireless communications system. Here a wireless device 142 such as a customer's smart phone communicates with the pharmacy's system 144 via the Internet depicted here as cloud 140. The pharmacy system 144 includes a server 120 connected to one or more pharmacist work stations 132 whereby each station typically includes a computer monitor, keyboard and mouse (not shown) which are further connected to a printer 134. The printer 134 can include the capabilities of printing a label which can thereafter be affixed to the prescription container, whereby the label could include information such as, but not limited to, directions for taking the medicine, the name of the medicine, the date of filling the prescription, an expiration date, dosages, the number of pills in the container, the name, address and phone number of the customer and the pharmacy, and the ID code. The printer could also print out a separate sheet of directions for taking the medicine, along with the ID code.

The pharmacy server 120 includes a receiving unit 122, a transmitting unit 124 and a database 126. The customer's medical data file 130 is stored in the server's database 126 which in turn is accessible by both the receiving unit 122 and the transmitting unit 124. The receiving unit 122 is equipped to receive data via wireless communications over the Internet from a wireless device 142 such as the customer's smart phone, whereby the received data includes the ID code to authenticate and establish communications between the wireless device 142 and the server 120. The received data can also include data to edit or add to the customer's medical data file 130. The transmitting unit 124 is equipped to send data via wireless communications over the Internet from the server to the wireless device 142, whereby the transmitted data can include portions of the customer's medical data file 130.

In FIG. 5, the customer or caregiver uses his smart phone 142 or another wireless device to connect over the Internet 140 to the pharmacy server 120 by providing authentication data to the server 120 by way of a security code, password or other known verification method. Once authenticated and connected to the pharmacy server, the customer or caregiver must either scan and send the customer ID code from the prescription container, or manually or otherwise enter the ID code to be sent from the wireless device 142 to the pharmacy server 120 to allow access to the customer's medical data file 130.

While specific embodiments have been shown and described, it should be understood by those skilled in the art that various changes in form and detail may be made therein.

What is claimed is:

1. A method for motivating proper prescription drug usage, the method comprising:
   receiving and filling a prescription of a medicine for a customer at a pharmacy by placing the medicine into a container and providing the customer with the container;
   assigning an ID code linked to a medical data file created and stored for the customer on a server for the pharmacy;
   providing instructions to the customer for taking the prescription medicine, wherein the instructions include the ID code and one or more predetermined tolerances for taking the medicine;
   providing a website wherein the pharmacy server is connected to the Internet via the web site;
   receiving and validating the ID code, via wireless communications, at the server from a customer's wireless device to access the customer's medical data file and to load a software application from the server to the customer's wireless device in response to a valid ID code;
   determining from the customer's medical file whether the prescription is valid or expired by having reached an end date of a prescription period;
   receiving compliance determination data from the customer's wireless device;
   determining compliance of the one or more predetermined tolerances from the received compliance determination data;
   controlling, by the server, a shell script on the wireless device by outputting a communication from the server to activate the software application on the customer's wireless device during the prescription period in response to (1) determination that the prescription is valid, and (2) determination of compliance; and
   controlling, by the server, a shell script on the wireless device by outputting a communication from the server to de-activate the software application on the customer's wireless device upon determination that an end of the prescription period during which the prescription is valid is reached, wherein during the prescription period the software application remains activated in response to a determination that the compliance determination data establishes a confirmation that the prescription medicine has been taken within a predetermined tolerance according to the instructions.

2. The method of claim 1 wherein the one or more predetermined tolerances comprise: a dosage of the medicine; a time frame for taking the medicine; whether to take the medicine with food or drink; and an expiration date of effectiveness of the medicine.

3. The method of claim 1 wherein the software application comprises one of: a gaming application; an entertainment application; an application allowing accessibility to an online service; an application allowing accessibility to special features of an online service; an application for watching movies; an application for watching videos; an application for listening to music; an application to enhance social network services; and an application to enhance online communications.

4. The method of claim 1 wherein notifications regarding the prescribed medicine are sent from the server to one or more of the customer; a pharmacist; a doctor; a nurse; a caregiver; an insurance company; a hospital; or another participant involved in the prescribing, distributing, maintaining, monitoring and administering of the medicine to the customer.

5. The method of claim 1 wherein the customer's medical data file includes: the customer's name, telephone number, email and postal address; the name and dosage of the medicine; the one or more predetermined tolerances for taking the medicine; a name and contact information of a doctor who prescribed the medicine; the customer's compliance determination data for taking the medicine; and the customer's prescription medicine history including compliance determination data for taking previously prescribed medicines.

6. The method of claim 1, further comprising the step of providing a report via wireless communications using a report application on the server that analyzes the customer's medical data file including the compliance determination data, and sending the report to one of the customer; a pharmacist; a doctor; a nurse; a caregiver; an insurance company; a hospital; or another participant involved in the prescribing, distributing, maintaining, monitoring and administering of the medicine to the customer.

7. The method of claim 1 further comprising the step of marking the instructions including the ID code onto the container, or onto a label to be affixed to the container, or onto a separate paper accompanying the container.

8. The method of claim 1 further comprising the step of authenticating that the wireless device is registered to the customer by receiving, at the pharmacy server, predetermined login data.

9. A method for motivating proper prescription drug usage, the method comprising the steps of:
receiving at a server for a pharmacy, via wireless communications from a wireless device, an ID code corresponding to a customer who has received prescription medicine from the pharmacy;
providing access by the wireless device to a medical data file of the customer on the server when the ID code is authenticated;
receiving compliance determination data from the wireless device to determine whether the customer is taking the prescription medicine in accordance with a predetermined schedule; and
controlling, by the server, a shell script on the wireless device by outputting a communication from the server to activate the shell script on the wireless device from the server in a prescription period that includes a duration of time during when the prescription medicine is valid and the shell script remains activated during the duration of time when the prescription medicine is valid when the compliance determination data indicates that the customer is taking the prescription medicine in accordance with the schedule, and further controlling, by the server, the shell script by outputting a communication from the server to de-activate the shell script on the wireless device when the compliance determination data indicates that the customer is not taking the prescription medicine in accordance with the schedule, wherein the shell script provides access to a software application, wherein during the prescription period the shell script remains activated in response to a determination that the compliance determination data establishes a confirmation that the prescription medicine has been taken within a predetermined tolerance according to the predetermined schedule.

10. The method of claim 9, wherein the software application is resident on the customer's wireless device, on the server or at another URL address available on the Internet.

11. The method of claim 9 further comprising authenticating that the wireless device is registered to the customer by receiving, at the pharmacy server, predetermined login data.

12. The method of claim 9 wherein the customer's medical data file includes: the customer's name, telephone number, email and postal address; the name and dosage of the medicine; the one or more predetermined tolerances for taking the medicine; a name and contact information of a doctor who prescribed the medicine; the customer's compliance determination data for taking the medicine; and the customer's prescription medicine history including compliance determination data for taking previously prescribed medicines.

13. The method of claim 9 wherein the software application comprises one of: a gaming application; an entertainment application; an application allowing accessibility to an online service; an application allowing accessibility to special features of an online service; an application for watching movies; an application for watching videos; an application for listening to music; an application to enhance social network services; and an application to enhance online communications.

14. The method of claim 9 further comprising the step of de-activating the shell script on the wireless device when the medicine is expired according to an expiration date in the medical data file.

15. The method of claim 9 wherein the wireless device is a smart phone, a computer, or a tablet.

16. The method of claim 9 wherein a report application on the server analyzes the medical data file including the compliance determination data and sends a report to one or more of the customer; a pharmacist; a doctor; a nurse; a caregiver; an insurance company; a hospital; or another participant involved in the prescribing, distributing, maintaining, monitoring and administering of the medicine to the customer.

17. The method of claim 9 wherein notifications regarding the prescribed medicine are sent from the server to one or more of the customer; a pharmacist; a doctor; a nurse; a caregiver; an insurance company; a hospital; or another participant involved in the prescribing, distributing, maintaining, monitoring and administering of the medicine to the customer.

18. A system for motivating proper prescription drug usage, the system comprising:
a server for providing computer services to a pharmacy for creating and storing a medical data file for a customer in a database on the server when a prescription for the customer is filled for a medicine into a container and supplying to the customer the prescription container along with an ID code linked to the customer's medical data file and instructions for taking the medicine;
a receiving unit connected to the server to receive data via wireless communications over the Internet from a wireless device of the customer, the received data including the ID code to authenticate and establish communications between the customer's wireless device and the server, wherein the received data further includes compliance determination data to determine whether the customer is taking the prescription medicine according to the instructions; and a transmitting unit connected to the server to transmit data via wireless communications over the Internet from the server to the customer's wireless device, the transmitted data including a shell script linked to a software application, wherein the transmitted data further includes data to control the shell script by outputting a communication from the server to activate the shell script on the customer's wireless device only in a prescription period that includes a duration of time during when the prescription medicine is valid and the shell script remains activated during the duration of time when the prescription medicine is valid when the compliance determination data indicates compliance in the customer taking the medicine, and data to control the shell script by outputting a communication from the server to de-activate the shell script on the customer's wireless device when the compliance determination data indicates non-compliance in the customer taking the medicine, wherein during the duration of time the software application remains activated in response to a determination that the compliance determination data establishes a confirmation that the prescription medicine has been taken within a predetermined tolerance according to the instructions.

19. The system of claim 18, wherein the software application is resident on the customer's wireless device, on the server or at another URL address available on the Internet.

20. The system of claim 18, further comprising a label marking device for marking the instructions onto the container, onto a label to be affixed to the container, or onto a separate paper accompanying the container of medicine.

* * * * *